(12) United States Patent
Ehr et al.

(10) Patent No.: US 8,430,924 B2
(45) Date of Patent: Apr. 30, 2013

(54) STENT CONFIGURATIONS

(75) Inventors: Timothy G. J. Ehr, Elk River, MN (US); Graig L. Kveen, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/048,474

(22) Filed: Mar. 15, 2011

(65) Prior Publication Data

US 2011/0166642 A1    Jul. 7, 2011

Related U.S. Application Data

(63) Continuation of application No. 10/832,768, filed on Apr. 27, 2004, now Pat. No. 7,905,912, which is a continuation of application No. 09/954,364, filed on Sep. 17, 2001, now Pat. No. 6,746,479, which is a continuation of application No. 09/389,832, filed on Sep. 3, 1999, now Pat. No. 6,334,870, which is a continuation of application No. 08/846,164, filed on Apr. 25, 1997, now Pat. No. 6,033,433.

(51) Int. Cl.
*A61F 2/06*    (2006.01)

(52) U.S. Cl.
USPC ........................................ 623/1.16

(58) Field of Classification Search ......... 623/1.11–1.54
See application file for complete search history.

(56) References Cited

U.S. PATENT DOCUMENTS

| | | | |
|---|---|---|---|
| 4,856,516 | A | 8/1989 | Hillstead |
| 4,994,071 | A | 2/1991 | MacGregor |
| 5,102,417 | A | 4/1992 | Palmaz |
| 5,104,404 | A | 4/1992 | Wolff |
| 5,116,365 | A | 5/1992 | Hillstead |
| 5,135,536 | A | 8/1992 | Hillstead |
| 5,195,984 | A | 3/1993 | Schatz |
| 5,382,259 | A * | 1/1995 | Phelps et al. ............ 606/151 |
| 5,383,892 | A | 1/1995 | Cardon et al. |
| 5,421,955 | A | 6/1995 | Lau et al. |
| 5,449,373 | A | 9/1995 | Pinchasik et al. |
| 5,514,154 | A | 5/1996 | Lau et al. |
| 5,540,701 | A | 7/1996 | Sharkey et al. |
| 5,549,663 | A | 8/1996 | Cottone, Jr. |
| 5,556,414 | A | 9/1996 | Turi |

(Continued)

FOREIGN PATENT DOCUMENTS

| | | |
|---|---|---|
| DE | 29615969 | 10/1996 |
| DE | 29701758 | 3/1997 |

(Continued)

OTHER PUBLICATIONS beStent™ sales brochure published by InStent Israel Ltd.

(Continued)

*Primary Examiner* — David Isabella
*Assistant Examiner* — Ann Schillinger
(74) *Attorney, Agent, or Firm* — Vidas, Arrett & Steinkraus, P.A.

(57) ABSTRACT

The invention is directed to an expandable stent which is longitudinally flexible in both the unexpanded and expanded conditions. The stent includes spiral structures which at least partially unwind upon expansion of the stent to limit stent recoil. Regions of low strain in the stent during expansion are provided by the spiral structures.

12 Claims, 11 Drawing Sheets

U.S. PATENT DOCUMENTS

| | | | |
|---|---|---|---|
| 5,575,816 A | 11/1996 | Rudnick et al. | |
| 5,607,442 A | 3/1997 | Fischell et al. | |
| 5,643,312 A | 7/1997 | Fischell et al. | |
| 5,697,971 A | 12/1997 | Fischell et al. | |
| 5,718,713 A | 2/1998 | Frantzen | |
| 5,725,572 A | 3/1998 | Lam et al. | |
| 5,733,303 A | 3/1998 | Israel et al. | |
| 5,755,781 A | 5/1998 | Jayaraman | |
| 5,759,174 A | 6/1998 | Fischell et al. | |
| 5,776,161 A * | 7/1998 | Globerman | 606/194 |
| 5,776,183 A | 7/1998 | Kanesaka et al. | |
| 5,800,519 A | 9/1998 | Sandock | |
| 5,817,126 A | 10/1998 | Imran | |
| 5,827,321 A | 10/1998 | Roubin et al. | |
| 5,843,168 A | 12/1998 | Dang | |
| 5,843,175 A | 12/1998 | Frantzen | |
| 5,868,781 A | 2/1999 | Killion | |
| 5,902,332 A | 5/1999 | Schatz | |
| 5,911,732 A | 6/1999 | Hojeibane | |
| 5,922,021 A | 7/1999 | Jang | |
| 6,022,371 A | 2/2000 | Killion | |
| 6,027,527 A | 2/2000 | Asano et al. | |
| 6,033,433 A | 3/2000 | Ehr et al. | |
| 6,042,597 A | 3/2000 | Kveen et al. | |
| 6,217,608 B1 | 4/2001 | Penn et al. | |
| 6,258,116 B1 | 7/2001 | Hojeibane | |
| 6,334,870 B1 | 1/2002 | Ehr et al. | |
| 6,746,479 B2 | 6/2004 | Ehr et al. | |
| 7,905,912 B2 | 3/2011 | Ehr | |
| 2002/0029079 A1* | 3/2002 | Kim et al. | 623/1.25 |
| 2002/0062149 A1 | 5/2002 | Jang | |

FOREIGN PATENT DOCUMENTS

| | | |
|---|---|---|
| DE | 29702671 | 4/1997 |
| DE | 29708689 | 7/1997 |
| DE | 29708879 | 7/1997 |
| EP | 0421729 | 4/1991 |
| EP | 0709067 | 5/1996 |
| EP | 0722700 | 7/1996 |
| EP | 0821921 | 2/1998 |
| JP | 3-045251 | 2/1991 |
| JP | 3-151983 | 6/1991 |
| JP | 7-178124 | 7/1995 |
| JP | 8-243107 | 9/1996 |
| JP | 8-336597 | 12/1996 |
| JP | 10-328312 | 12/1998 |
| JP | 2001-509702 | 7/2001 |
| WO | 9603092 | 2/1996 |
| WO | 9626689 | 9/1996 |
| WO | 9732543 | 9/1997 |
| WO | 9732544 | 9/1997 |
| WO | 9733534 | 9/1997 |
| WO | 9833546 | 8/1998 |
| WO | 9835634 | 8/1998 |
| WO | 9853763 | 12/1998 |

OTHER PUBLICATIONS

Notice of Opposition dated Dec. 10, 2004 and English translation.
PCT International Search Report for related Foreign application, Aug. 3, 1998.
Online excerpt from Brockhaus Naturwissenschaften and Technik, Mannheim, and Spektrum Akademischer Verlag GmbH Heidelberg 2003.
Handbook of Coronary Stents, Second Edition, Rotterdam Thorazcenter Group, edited by Patrick W. Serruys, Michal JB Kutryk, published in 1998, p. 203-212, describing the "divYsio sten!".
Handbook of Coronary Stents, Second Edition, Rotterdam Thoraxcenter Group, edited by Patrick W. Serruys, Michal JB Kutryk, published in 1998, p. 187-201, describing the "JOSTENT coronary stent range".
Handbook of Coronary Stents, Rotterdam Thoraxcenter Group, editor-in-ChiefPatrick W. Serruys, published in 1997, p. 153-163, describing the "BeStent".
Notice of Opposition dated Dec. 11, 2004.
Communication in EP Opposition from Vossius & Partner to EPO regarding Application No. 989198741, dated Aug. 22, 2012.
Communication in EP Opposition pursuant to Article 101(1) and Rule 81(2) to (3) EPC from EPO regarding Application No. 98919874.2, dated Sep. 21, 2011.
Reference A1 from EP Opposition Proceedings in Application No. 98919874.2.
Reference A2 from EP Opposition Proceedings in Application No. 98919874.2.
Communication in EP Opposition Proceedings from Ter Meer Steinmeister & Partner regarding Application No. 98919874.2, dated Aug. 26, 2008.
Appeal filed by Vossius & Partner on Aug. 7, 2008, requesting that the decision to revoke European Patent No. EP-B-979059 be reversed.
Communication from Opposition Division Revoking the EP Patent EP-B-979059, dated Apr. 15, 2008, Apr. 24, 2008 and May 29, 2008.
Communication in EP Opposition Proceedings from Eisenfuhr, Speiser & Partner regarding Application No. 98919874.2, dated Mar. 14, 2008.
Response filed by Vossius & Partner, on Mar. 12, 2008, to Preliminary Opinion of EP Opposition Division regarding Application No. 98919874.2.
Communication from EPO regarding Opposition proceedings for Application No. 98919874.2, dated Oct. 24, 2007.
Communication filed by Vossius & Partner with EPO on Jan. 17, 2007 regarding EP Opposition proceedings for Application No. 98919874.2.
Communication filed by Ter Meer Steinmeister & Partner with EPO on Apr. 3, 2006 regarding EP Opposition proceedings for Application No. 98919874.2.
Response, filed by Vossius & Partner with EPO on Sep. 14, 2005, to Communication of Notices of Opposition for Application No. 98919874.2.
Communication from EPO, dated Mar. 29, 2012, regarding EP Opposition proceedings for EP Application No. 98919874.2.
Brief Communication from EPO, dated Feb. 8, 2012, including response filed by Ter Meer Steinmeister & Partner on Jan. 30, 2012 in EP Opposition proceedings for Application No. 98919874.2.
Brief Communication from EPO, dated Nov. 3, 2011, including response filed by Vossius & Partner on Oct. 27, 2011 in EP Opposition proceedings for Application No. 98919874.2.
Communication from Ter Meer Steinmeister & Partner to EPO regarding EP Opposition proceedings for Application No. 98919874. 2, dated Sep. 23, 2011.
Decision on the Technical Boad of Appeal, dated May 17, 2011, including decision dated Mar. 9, 2011 regarding EP Opposition proceedings for Application No. 98919874.2.
Minutes of the public oral proceedings before the Technical Board of Appeal, dated Mar. 15, 2011, regarding EP Opposition proceedings for Application No. 98919874.2.
Communication from EPO, dated Feb. 14, 2011, to Eisenfuhr, Speiser & Partner, including a response to the Summons from Vossius and Partner, dated Feb. 9, 2011, regarding EP Opposition proceedings for Application No. 98919874.2.
Reply from Vossius & Partner, dated May 28, 2009, regarding EP Opposition proceedings for Application No. 98919874.2.
Communication from Eisenfuhr, Speiser & Partner to EPO, dated Mar. 13, 2009, regarding EP Opposition proceedings for Application No. 98919874.2.
Communication from Ter Meer Steinmeister & Partner to EPO, dated Feb. 2, 2009, regarding EP Opposition proceedings for Application No. 98919874.2.
Written statement setting out Grounds of Appeal from Vossius & Partner to EPO, dated Sep. 16, 2008, regarding EP Opposition proceedings for Application No. 98919874.2.
Reference A3 from EP Opposition Proceedings in Application No. 98919874.2.
Reference A4 from EP Opposition Proceedings in Application No. 98919874.2: Printout from European Online Patent Register regarding reference D7.
Non-Final Office Action mailed Jul. 18, 2011 for U.S. Appl. No. 12/192,782.

Amendment, dated Nov. 4, 2011, in response to Non-Final Office Action for U.S. Appl. No. 12/192,782.
Final Office Action mailed Dec. 15, 2011 for U.S. Appl. No. 12/192,782.
Amendment, dated Feb. 9, 2012, in response to Final Office Action for U.S. Appl. No. 12/192,782.
Advisory Office Action mailed Feb. 17, 2012 for U.S. Appl. No. 12/192,782.
Pre-Appeal Conference Brief filed Mar. 13, 2012 for U.S. Appl. No. 12/192,782.
Panel Decision from Pre-Appeal Brief Review, mailed Apr. 11, 2012, for U.S. Appl. No. 12/192,782.
Appeal Brief filed Jul. 13, 2012 for U.S. Appl. No. 12/192,782.
Examiners Answer mailed Aug. 20, 2012 for U.S. Appl. No. 12/192,782.
Reply Brief filed Oct. 4, 2012 for U.S. Appl. No. 12/192,782.
Communication from Opponent in response to the Summons to attend the Oral Proceedings, dated Nov. 9, 2012.
Communication from EPO regarding the results of the oral proceedings, dated Dec. 13, 2012.
Communication from EPO, dated Jan. 16, 2013.

* cited by examiner

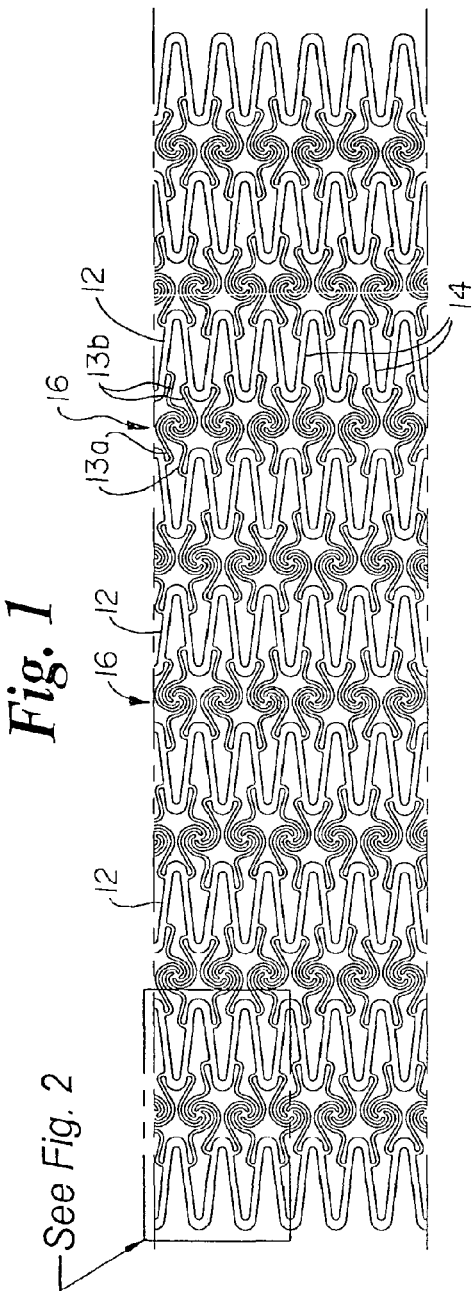
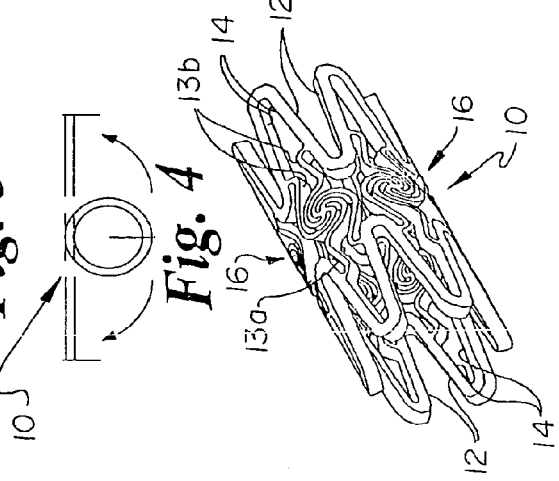
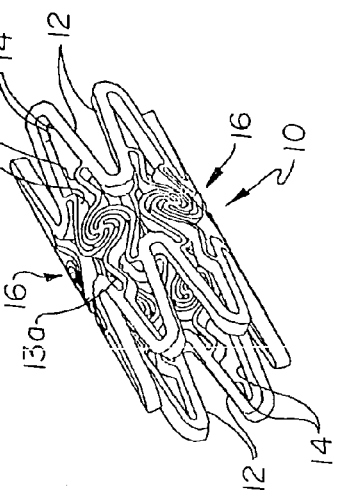
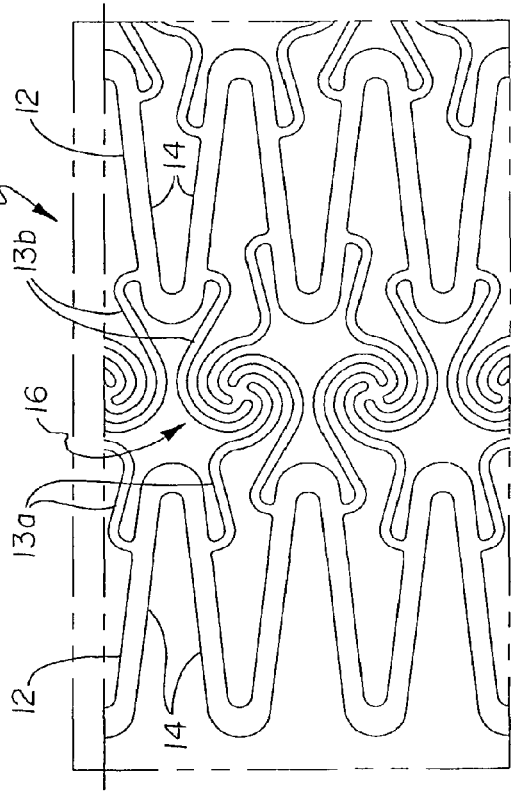

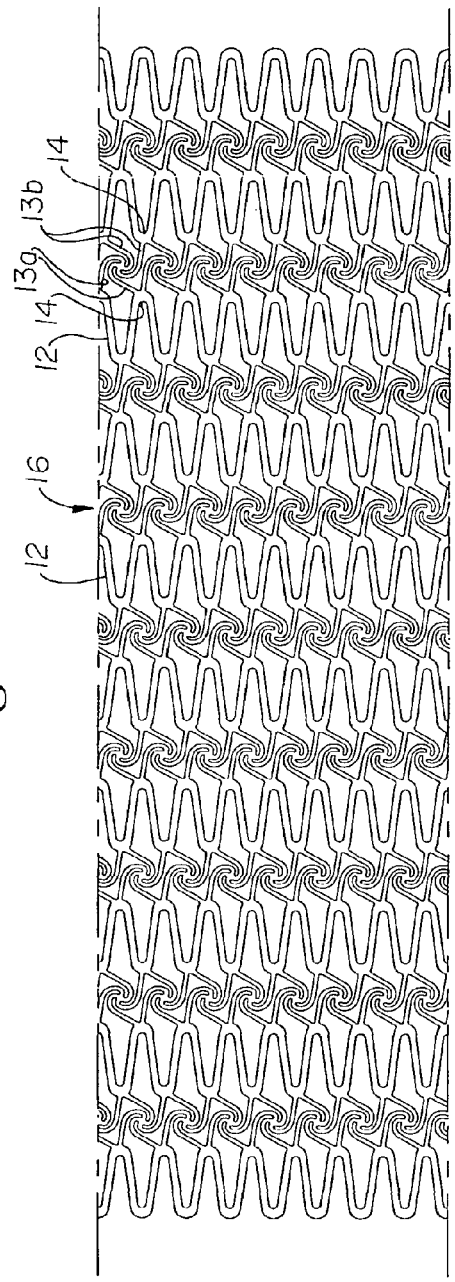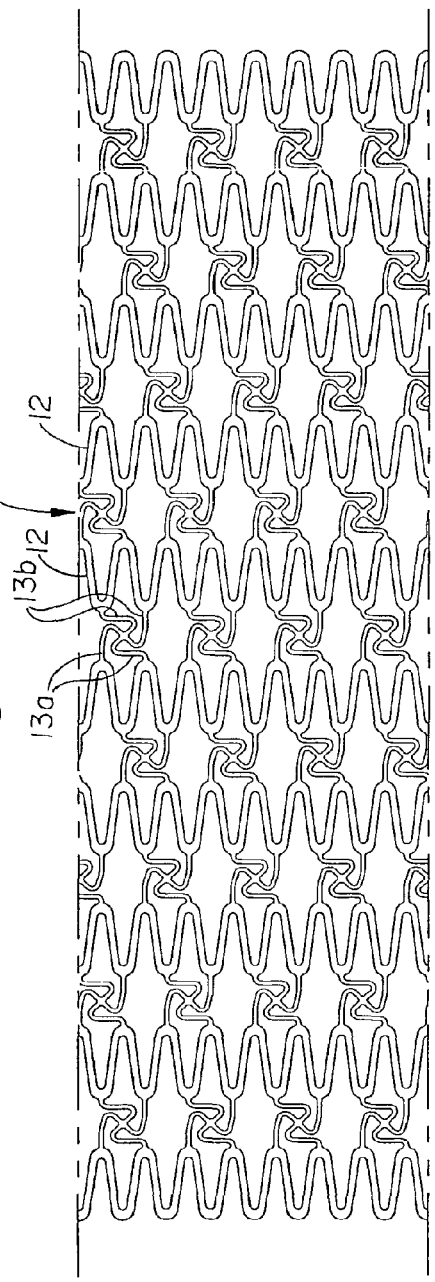

STENT CONFIGURATIONS

CROSS-REFERENCE TO RELATED APPLICATIONS

This application is a Continuation application of U.S. application Ser. No. 10/832,768, filed Apr. 27, 2004, which is a continuation of U.S. application Ser. No. 09/954,364, filed Sep. 17, 2001, issued as U.S. Pat. No. 6,746,479, which is a Continuation of U.S. application Ser. No. 09/389,832, filed Sep. 3, 1999, issued as U.S. Pat. No. 6,334,870, which is a continuation of U.S. application Ser. No. 08/846,164, filed Apr. 25, 1997, issued as U.S. Pat. No. 6,033,433, the contents of which are hereby incorporated by reference.

BACKGROUND OF THE INVENTION

1. Field of the Invention

This invention relates to stents of improved configuration which incorporate spiral articulations which unwind to form bracing structures or scaffolding upon expansion.

2. Brief Description of the Prior Art

Stents are radially expandable endoprosthesis which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

In the past, stents have assumed many configurations and been made of many materials, including metals and plastic. Ordinary metals such as stainless steel have been used as have shape memory metals such as nitinol and the like. Stents have also been made of biodegradable plastic materials. They have been formed from wire, tube stock, etc.

SUMMARY OF THE INVENTION

This invention provides a new configuration for stents which may be adapted by all of the various types of prior art stents referred to hereinabove. There are numerous advantages to the new configuration. It limits recoil and adds resistance to compression for the expanded stent, among other things. It is longitudinally flexible in both the unexpanded and expanded conditions. It has several embodiments.

An important part of the new configuration includes a spiral or spiral-like structure comprised of joined elements which are coiled or bent and which unwind, uncoil or unbend to a more or less straightened condition on expansion of the stent. Such structures are hereinafter referred to collectively as spirals, spirals or spiral-like structures. These structures provide regions of low strain in the stent during expansion. These elements may be joined to each other or to any radially expansive members of any kind, annular serpentine members being preferred.

BRIEF DESCRIPTION OF THE FIGURES

FIG. 1 is a flat view of one pattern embodiment of a stent configuration of the invention (unexpanded);

FIG. 2 is a detail of a portion of FIG. 1;

FIG. 3 is an end view of a stent of the FIG. 1 pattern according to the invention showing it in tubular configuration;

FIG. 4 is a showing of a stent in the embodiment of the preceding Figures in perspective and in an unexpanded configuration;

FIG. 9 is a plan view showing another embodiment of the invention;

FIG. 10 is a showing of a modified embodiment;

DETAILED DESCRIPTION OF THE PREFERRED EMBODIMENTS

Figure 6:
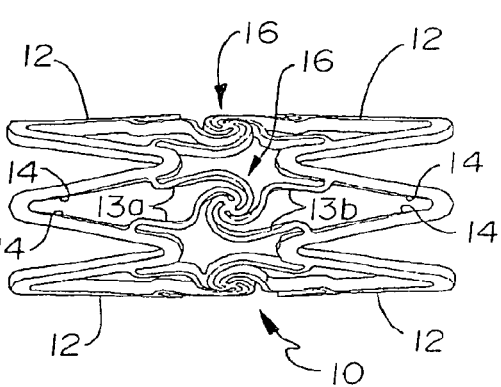
FIGS. 6, 7 and 8 are showings of the stent of FIG. 4 in various stages of expansion with only details of the front of the stent shown for simplicity.
Figure 7:
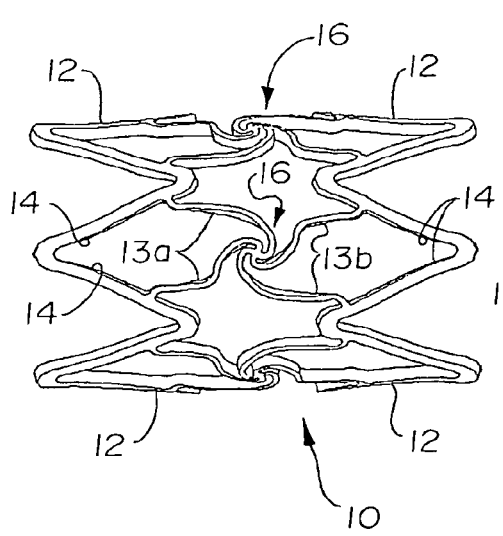
Figure 8:
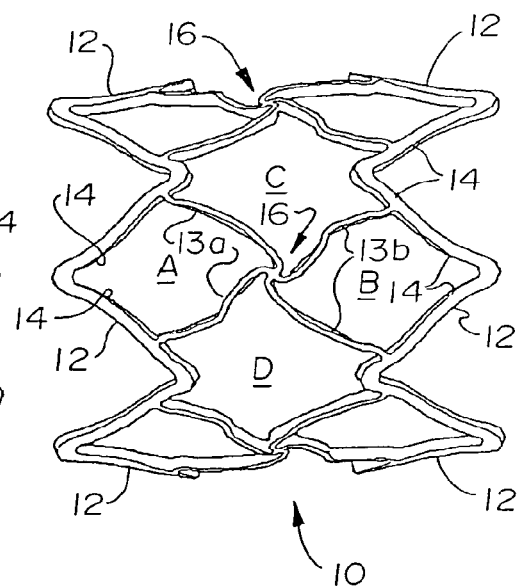

One preferred embodiment of the invention is illustrated in FIGS. 1-8. It comprises a metal tube-like structure 10 as best shown in FIGS. 3 and 4, such as nitinol or stainless steel, which has been etched or laser cut to the configuration shown in the plan view of FIGS. 1 and 2 and in a short version as shown in FIG. 4. The configuration is made up of a series of serpentine annular expandable elements or segments 12 which form loops 14 to allow for radial annular expansion. Segments 12 may be other configurations but serpentine is preferred. Elements 12 are interconnected by pairs of elongated members 13a and 13b which are attached at one end to successive loops 14 of a segment 12 and which are joined at their other ends to adjacent pairs of elongated members 13a and 13b, as best seen in detail in FIG. 2. Members 13a and 13b are preferably of narrower gauge than members 12 and are joined together in a coiled or spiral arrangement as shown generally at 16. Spiral 16 forms a structure about which members 13 may uncoil or unwind in a counterclockwise direction or clockwise direction to a substantially straight condition, depending on the spiral winding direction, upon radial expansion of members 12. In this embodiment spirals 16 are formed in alternate wound structures so that some unwind in one direction and some in the other direction. Of course, in any embodiment the spirals can be formed so that they all unwind in one direction, either clockwise or counterclockwise and they may have more or fewer members 13. Also, more or less spirals may be included between the segments. The unwinding is accompanied by a straightening action with respect to members 13 as is described in more detail in connection with FIGS. 4-8. It can be seen from FIGS. 4 through 8 that the resultant configuration in an expanded stent of this configuration is comprised of a plurality of cells, the perimeter of each of which is defined by a pair of members or struts defined by the loop portion 14 of segment 12 and a pair of members or struts 13. The cells are joined at 16 as best seen in FIG. 8. More specifically the cells are of two kinds as shown in FIG. 8. A first pair of cells are A and B made up of a segment 12 and two struts 13a for cell A or 13b for cell B. A second pair of cells are C and D made up of an inward loop portion 14 of segment 12 and a strut 13a and a strut 13b for cells C and D.

Figure 5:
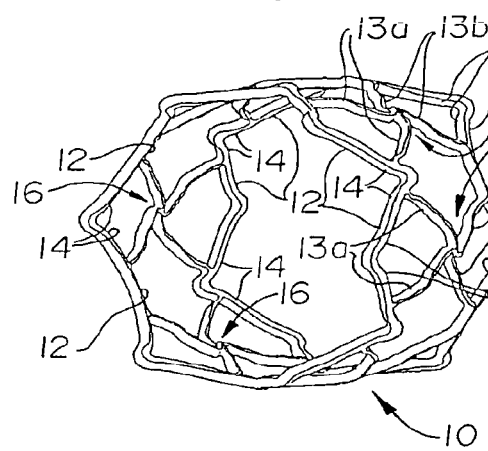
FIG. 5 is a showing of the stent of FIG. 4 fully expanded with details of the front and rear of the stent.

When a stent of the invention, such as that shown in FIGS. 1-4 undergoes expansion, such as from the embodiment of FIG. 4, it will appear as shown in FIG. 5 in the fully expanded condition. FIG. 5 shows the stent in perspective.

The unwinding action which the coil elements 16 undergo upon stent expansion is best seen in FIGS. 6-8 which show only the front side surface of the stent for simplicity and clarity.

As radial expansion begins (seen in FIG. 6) it can be appreciated that the spiral elements 16 undergo an unwinding or straightening action by a pulling force on all of the members 13. Specifically, as expansion occurs, elements 13 undergo a straightening action as can be seen in the early stages of expansion in FIG. 6.

Upon further expansion (seen in FIG. 7), spirals 16 undergo further unwinding, i.e., elements 13 undergo further straightening.

Finally in FIG. 8, substantial full expansion provides substantially straightened elements 13 which in that condition limit stent recoil and increase the resistance to compression of the stent.

FIG. 9 shows a modified embodiment in which elements 13a and 13b contact segment 12 at the end of its loops 14. Also note in this embodiment that the spirals 16 are all wound in the same direction.

FIG. 10 shows an embodiment of the invention in which the spiral members 13 are more bent and less curvilinear but still form a spiral-like configuration 16. The remainder of the configuration is similar to that of FIG. 9. In FIG. 10, elongate members 13 are shown prior to expansion of the stent. When the stent is expanded, members 13 unwind counter-clockwise and straighten somewhat. At full expansion members 13 straighten still further and straighten substantially so as to provide resistance to compression of the stent and low recoil. The expanded configuration displays a cell configuration similar to that seen in FIG. 8.

Figure 11:
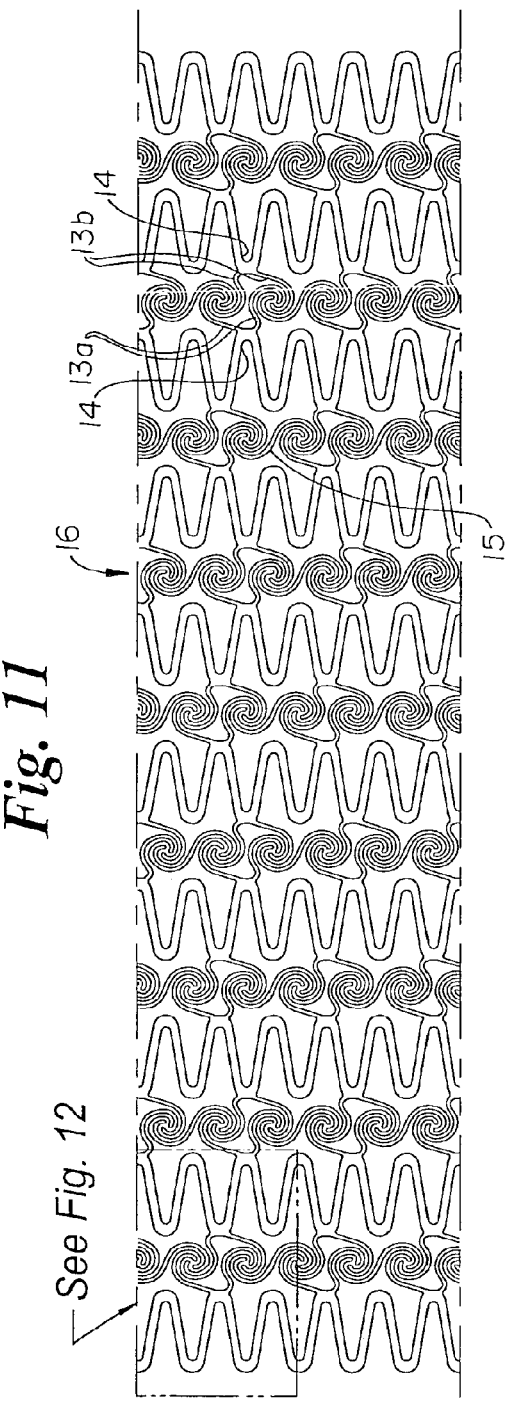
FIG. 11 is a showing of another embodiment.
Figure 12:
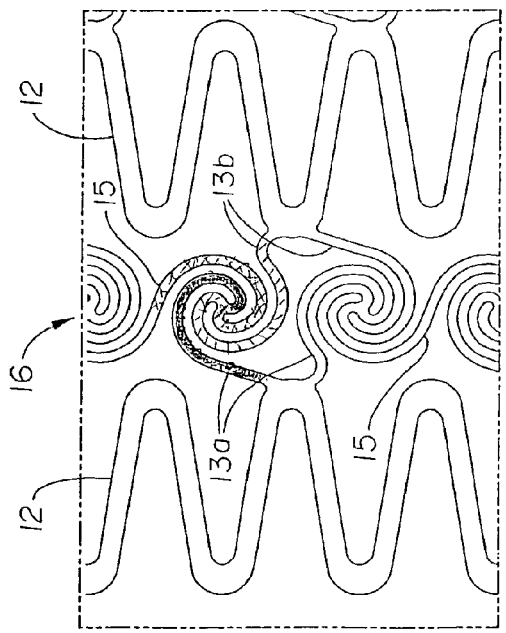
FIG. 12 is a detail of a portion of FIG. 11.
Figure 13:
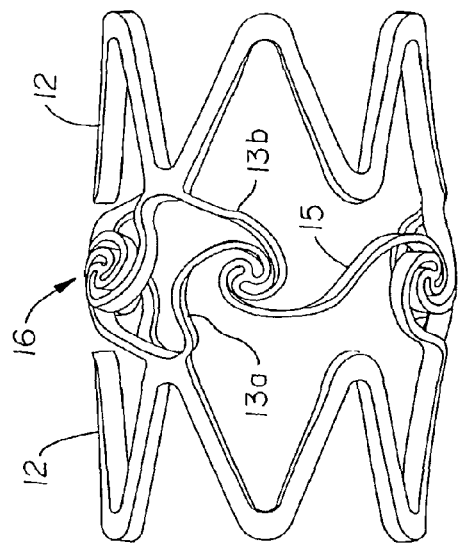
FIG. 13 is a showing of the stent of FIGS. 11 and 12 in an expanded configuration.

Other embodiments are shown in subsequent Figures with different spiral arrangements. For example, the embodiment of FIGS. 11-13 shows coiled arrangements 16 which are wound in the same direction and elements 13 attached at the end of loops 14 while some adjacent spirals between segments are interconnected by members 15.

Figure 14:
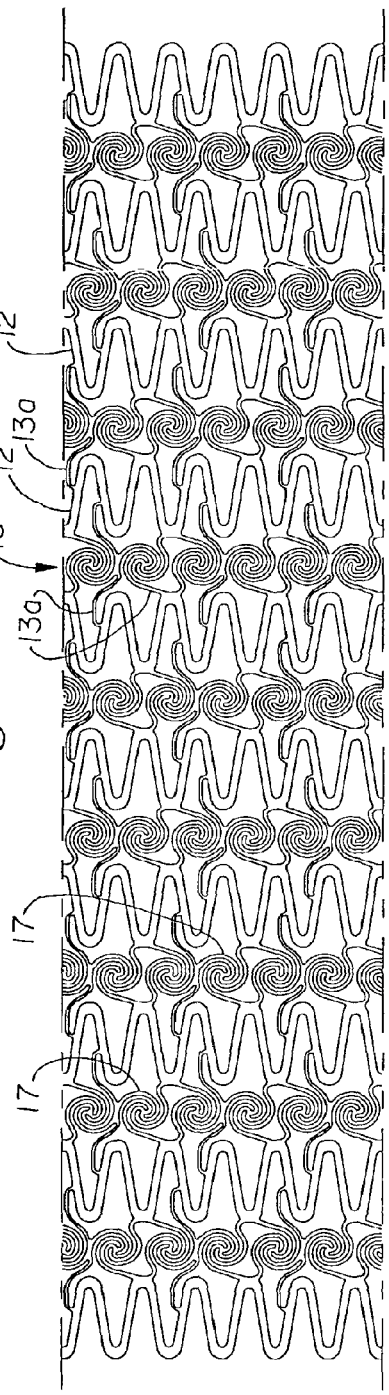
FIG. 14 is a showing of another embodiment.

FIG. 14 shows some elements 13 in a spiral 16 contacting the end of loops 14 and some contacting segment 12 proper. Also, some adjacent spirals are interconnected by members 17.

Figure 15:
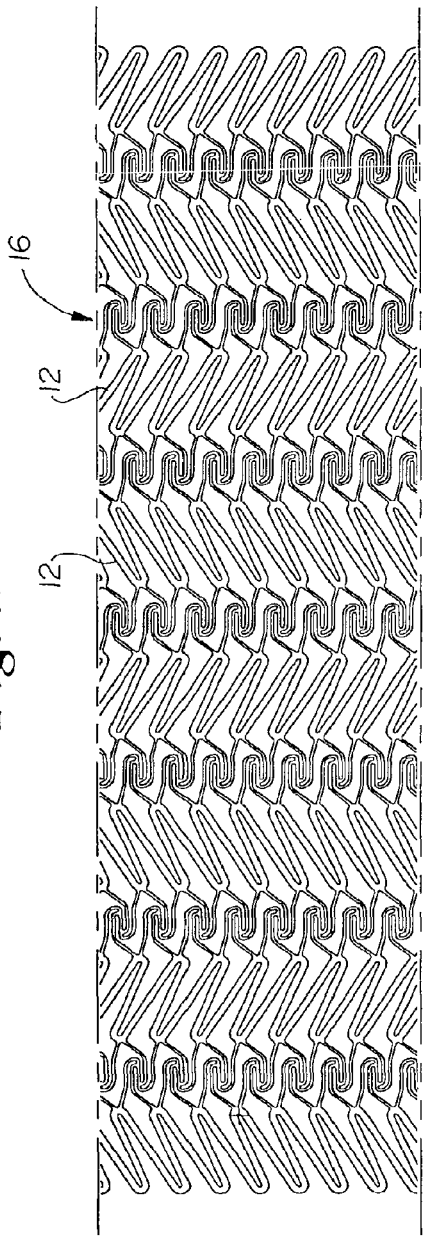
FIG. 15 is a showing of still another embodiment.

FIG. 15 shows a flattened or elongated spiral arrangement 16 and elements 12 are angled with respect to the longitudinal axis of the stent. In previous embodiments, these elements or segments have been arranged parallel to the axis or horizontal. Elongated spirals as in FIG. 13 and spirals of previous Figures may be mixed together. (Not shown).

Figure 16:
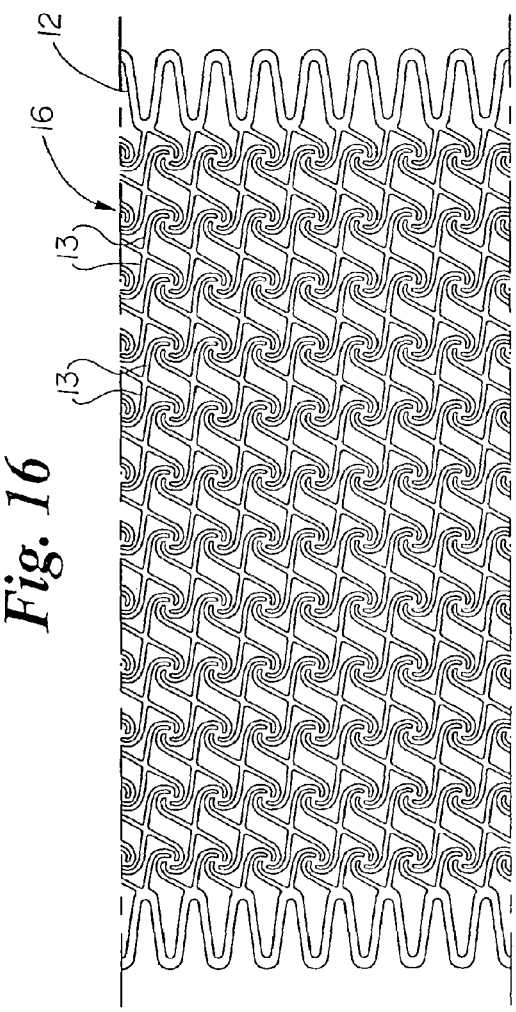
FIG. 16 is a showing of yet another embodiment.

In the embodiments already discussed, annular expandable segments such as segments 12 are interspersed with spiral arrangements 16. However, as can be seen in FIG. 16, at least a substantial portion or all of the stent body can be merely comprised of spiral arrangements 16 connected to each other. Actually, all of the body may consist of spirals. In this embodiment, the elements 13 interconnect between spirals over substantially the entire body of the stent. Optionally, the ends may include segments 12 as shown.

Figure 17:
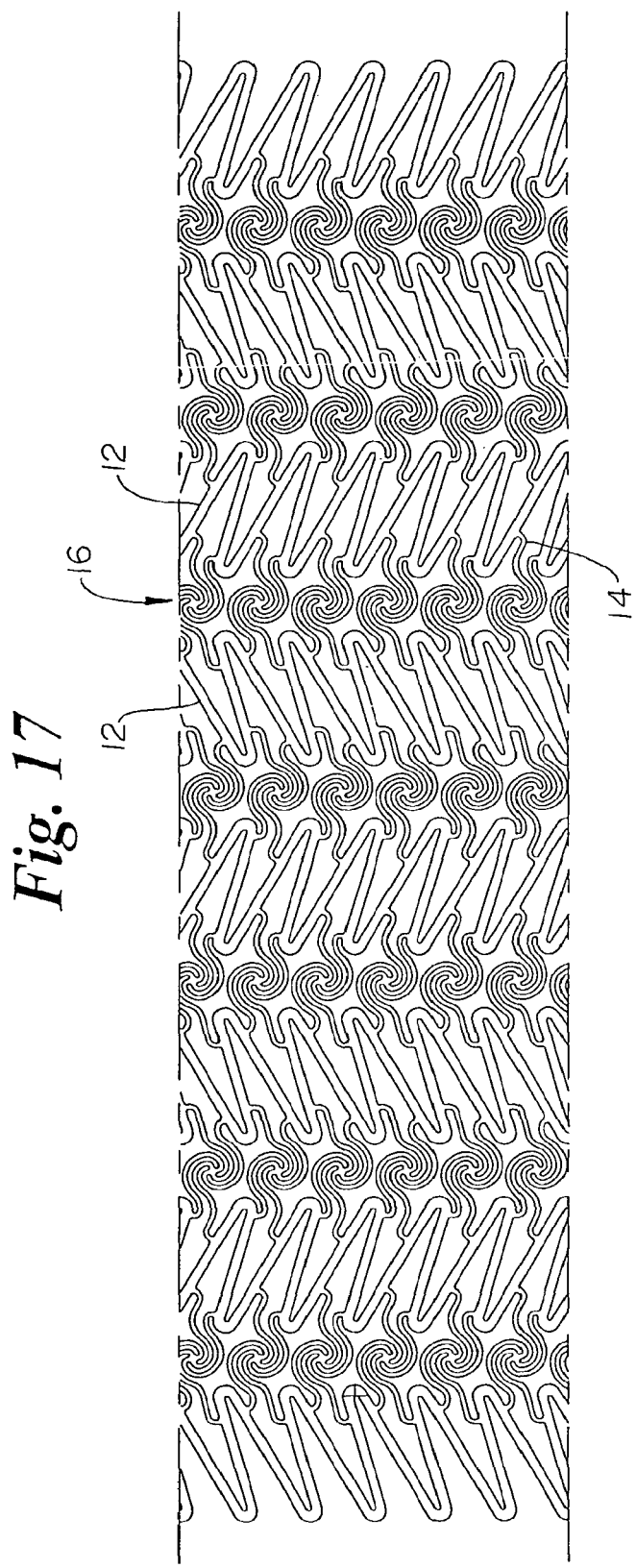
FIG. 17 is a showing of still another embodiment.
Figure 18:
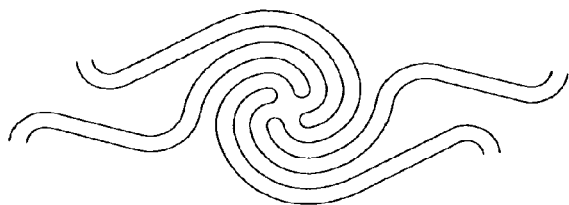
FIGS. 18-28 show various spiral-like arrangements of the invention.
Figure 19:
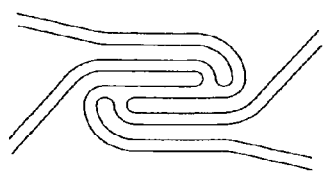
Figure 20:
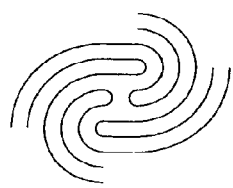
Figure 21:
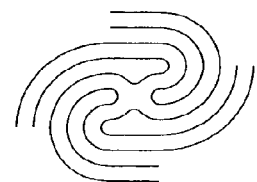
Figure 22:
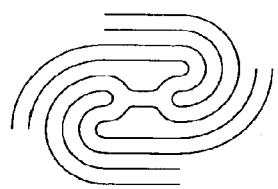
Figure 23:
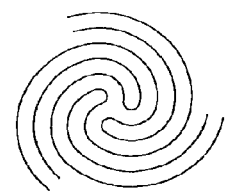
Figure 24:
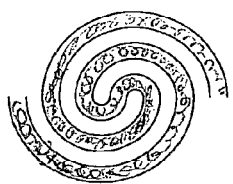
Figure 25:
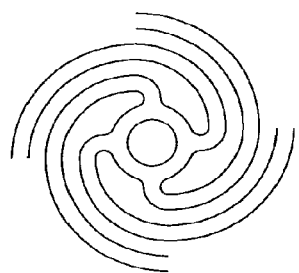
Figure 26:
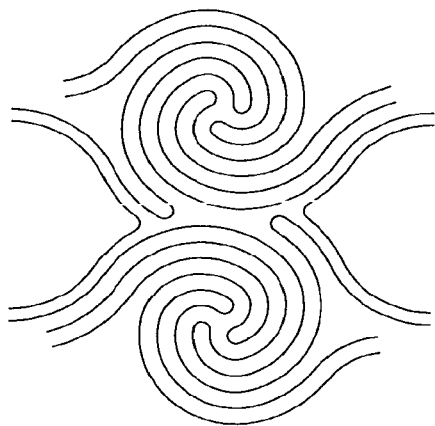
Figure 27:
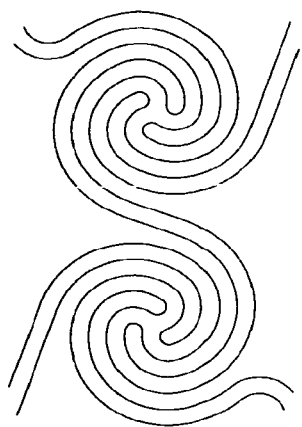
Figure 28:
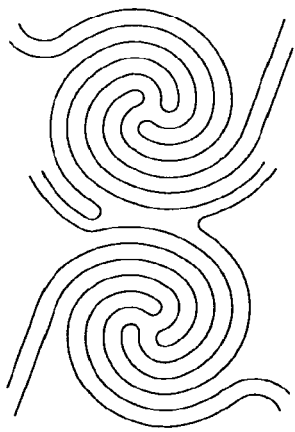

The embodiment shown in FIG. 17 shows segments 12 alternately angled in opposite directions and with legs thereof of different length and elements 13 contacting the segments at different locations, i.e., as at the loop portion 14 and at the segment portion proper.

FIGS. 18-28 demonstrate examples of what is meant by the terms spiral and spiral-like herein. Of course, additional members may be included in the spirals.

Figure 29:
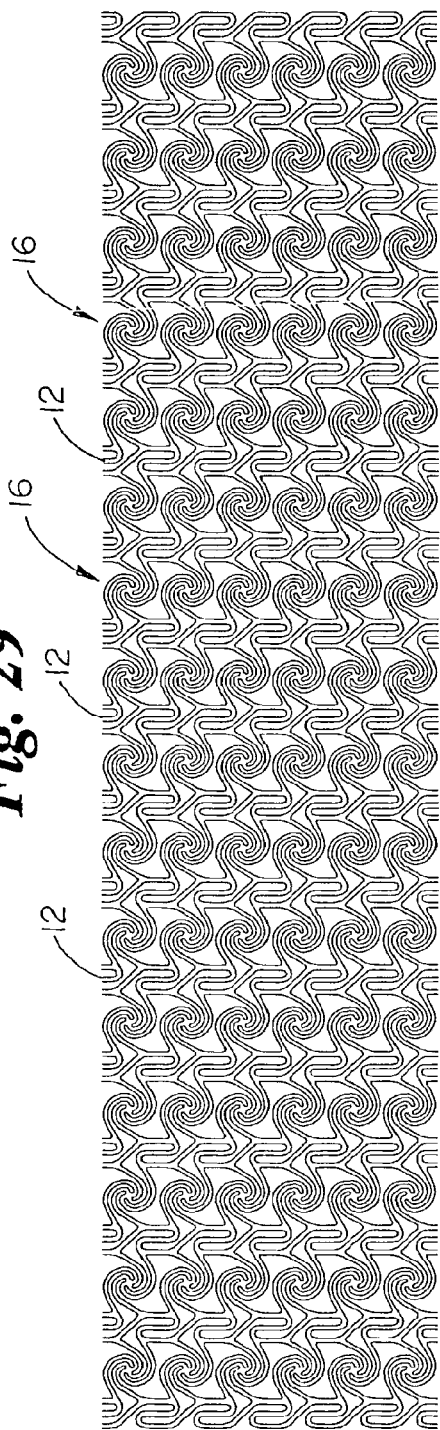
FIG. 29 shows another embodiment of the invention.

FIG. 29 shows segments 12 in a configuration other than the annular serpentine configuration of previous Figures.

Figure 30:
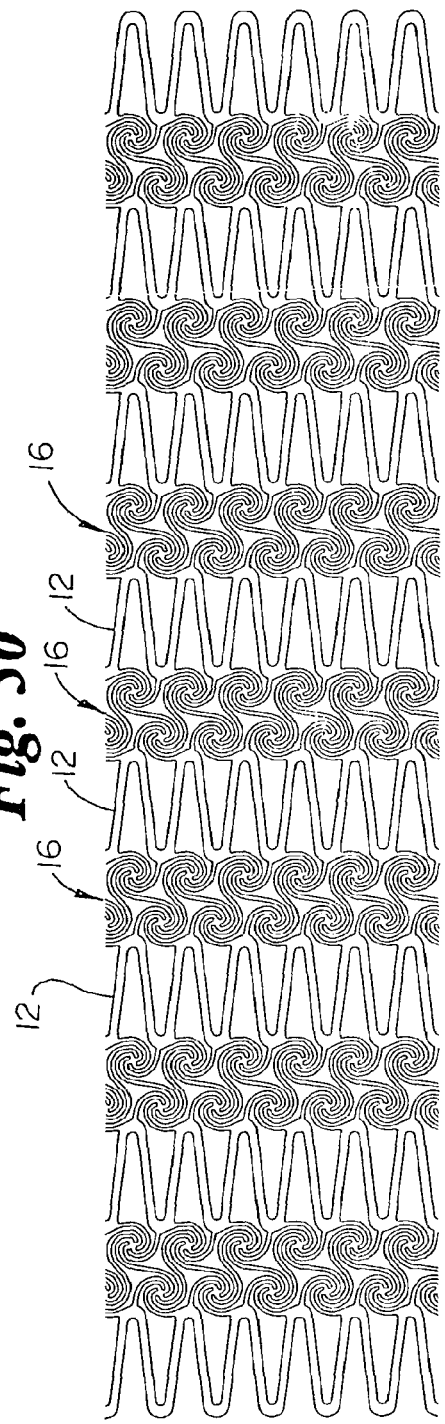
FIG. 30 shows yet another embodiment.

FIG. 30 shows alternate segments 12 in serpentine annular configuration interconnected by double rows of interconnected coil configurations 16.

Figure 31:
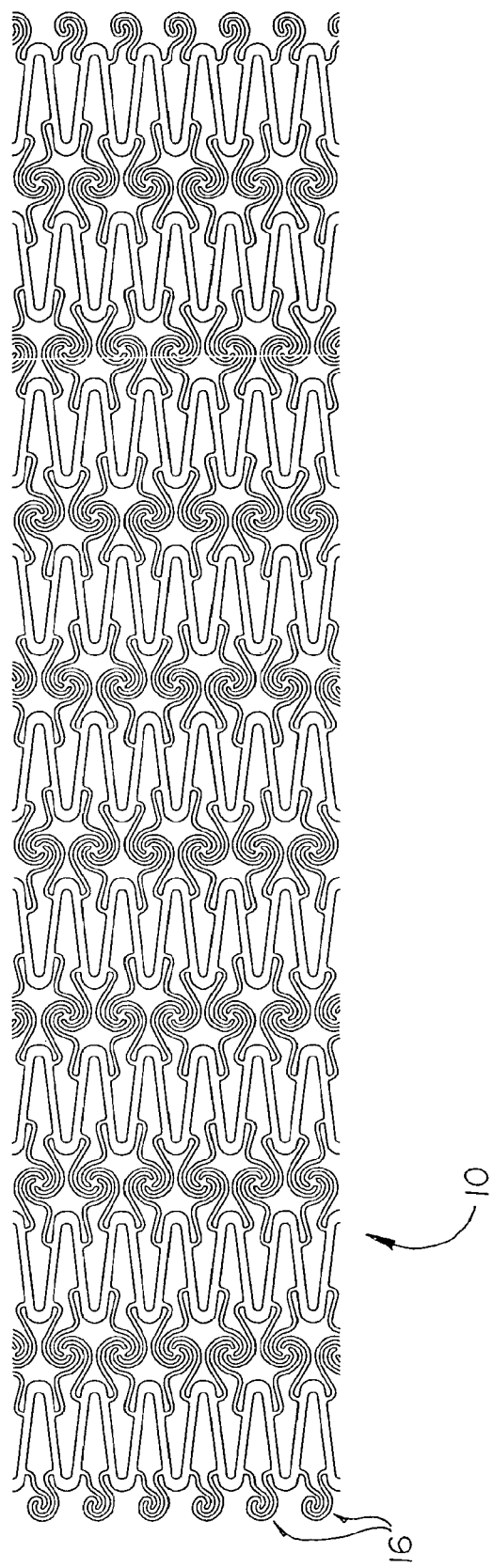
FIG. 31 shows still another embodiment of the invention.

FIG. 31 is included to demonstrate that spirals 16 may be included on the ends of a stent 10.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent comprising:
a plurality of serpentine annular expandable elements each comprising a plurality of straight segments interconnected by curved segments, the straight segments having a straight segment width; and
a plurality of connector columns, each of the connector columns comprising a plurality of connectors, each connector comprising at least one coiled segment, the coiled segment having a coiled segment width that is less than the straight segment width;
wherein the serpentine annular expandable elements are interconnected by the connector columns.

2. The stent of claim 1, wherein each straight segment has a first end and a second end, the curved segments extending from and connecting adjacent straight segments.

3. The stent of claim 1, wherein each connector is connected to four curved segments.

4. The stent of claim 1, wherein each connector is connected to four straight segments.

5. The stent of claim 1, wherein each connector is connected to an adjacent connector.

6. The stent of claim 1, wherein each connector is connected to an adjacent connector and at least one curved segment.

7. The stent of claim 1, wherein each connector is connected to an adjacent connector, a curved segment, and a straight segment.

8. The stent of claim 1, wherein the plurality of connectors comprises first connectors and second connectors, the first connectors coil in a first direction and the second connectors coil in a second direction opposite the first direction.

9. The stent of claim 1, wherein the connectors of the plurality of connectors coil in the same direction.

10. The stent of claim 1 further comprising a longitudinal axis, wherein the straight segments are perpendicular to the longitudinal axis.

11. The stent of claim 1, wherein the connectors of each connector column are arranged in double rows.

12. The stent of claim 1, wherein each of the connectors has three arms.

* * * * *